US009456879B2

(12) United States Patent
Breguet

(10) Patent No.: US 9,456,879 B2
(45) Date of Patent: Oct. 4, 2016

(54) ENDODONTIC INSTRUMENT FOR DRILLING

(75) Inventor: Olivier Breguet, Le Locle (CH)

(73) Assignee: FKG Dentaire S.A., La Chaux-de-Fonds (CH)

(*) Notice: Subject to any disclaimer, the term of this patent is extended or adjusted under 35 U.S.C. 154(b) by 5 days.

(21) Appl. No.: 14/005,578

(22) PCT Filed: Mar. 13, 2012

(86) PCT No.: PCT/CH2012/000057
§ 371 (c)(1),
(2), (4) Date: Sep. 17, 2013

(87) PCT Pub. No.: WO2012/126128
PCT Pub. Date: Sep. 27, 2012

(65) Prior Publication Data

US 2014/0004480 A1 Jan. 2, 2014

(30) Foreign Application Priority Data

Mar. 18, 2011 (CH) ........................................ 465/11

(51) Int. Cl.
*A61C 5/02* (2006.01)

(52) U.S. Cl.
CPC .................................... *A61C 5/023* (2013.01)

(58) Field of Classification Search
CPC ............ A61C 5/023; B23B 2251/245; B23B 2251/04
USPC .......................................................... 433/102
See application file for complete search history.

(56) References Cited

U.S. PATENT DOCUMENTS

2004/0219484 A1* 11/2004 Scianamblo ........... A61C 5/023 433/102
2012/0021376 A1* 1/2012 Iwamoto et al. ............. 433/102
2012/0208146 A1* 8/2012 Mordeniz .............. A61O 5/023 433/102

FOREIGN PATENT DOCUMENTS

AE WO 2012114052 A1 * 8/2012 ............. A61C 5/023
EP 1 752 109 A1 2/2007
FR 339904 A * 6/1904 ............. B23B 51/02
JP WO 2010098385 A1 * 9/2010 ............. A61C 5/023
WO 2007/016278 A1 2/2007

(Continued)

OTHER PUBLICATIONS

International Search Report Corresponding to PCT/CH2012/000057 mailed Sep. 27, 2012.

*Primary Examiner* — Nicholas Lucchesi
*Assistant Examiner* — Matthew Saunders
(74) *Attorney, Agent, or Firm* — Davis & Bujold PLLC; Michael J. Bujold

(57) ABSTRACT

An endodontic instrument for drilling root canals, in particular a flexible drilling instrument which includes a working part and a securing end fitting intended for mounting the instrument in a mandrel of a contra-angle-type support provided with an electric motor used to drive an instrument clockwise. The casing of the working part is conical along its length and ends in a tip. The working part is provided with a spiral flute forming a ridge having a cutting edge. The drill bit, relief and cutting angles defined by the cutting edge can be varied along the length of the working part so that the instrument is particularly sharp in the area near the tip and so that the profile of the cutting ridge becomes progressively more blunt along the length of the instrument.

12 Claims, 12 Drawing Sheets

(56) References Cited

FOREIGN PATENT DOCUMENTS

| | | | | |
|---|---|---|---|---|
| WO | 2011/042662 | A1 | | 4/2011 |
| WO | WO 2011/042662 | A1 | * | 4/2011 |
| WO | WO2011/042662 | A1 | * | 4/2011 |

* cited by examiner

ENDODONTIC INSTRUMENT FOR DRILLING

This application is a National Stage completion of PCT/CH2012/000057 filed Mar. 13, 2012 , which claims priority to Swiss patent application ser. no. 465/11 filed Mar. 18, 2011.

FIELD OF THE INVENTION

The present invention concerns an endodontic instrument for drilling root canals, particularly a flexible drilling instrument, the instrument having a longitudinal rotational axis and comprising a portion called the working portion, terminating in a tip at one extremity and at the other extremity in a securing end fitting that can be attached to a mandrel driven by an electric motor, the working portion comprising at least one spiral flute defining at least one ridge comprising an edge with a peak and two sides, exterior and interior, respectively, located on either side of the edge, the edge peak being situated on a circle whose center is located on the instrument's longitudinal axis of rotation.

BACKGROUND OF THE INVENTION

Cleaning and shaping root canals for receiving filling substance is accomplished using drilling instruments which have a conical active portion called the working portion that comprises several cutting edges arranged in a spiral along the working portion.

An example of this type of dental instrument is illustrated by International Publication No. WO 2007/016278 A1 which describes a generally conical endodontic instrument comprising several spiral flutes with variable spaces between the spirals according to the sectors of the active portion. These instruments, called endodontic files, are designed for manual or mechanized use. When the endodontic files are driven by an electric motor they rotate at a slow speed (for example between 150 and 600 rotations per minute) and progress through the canal opening in such a way that their active area can cut or scrape the walls of the root canal. Areas that were reduced in length at the beginning of the intervention extend farther and farther as the files advance through the canals. The drive torque that must be applied to the files in order to overcome the increasing force of friction and to make the files turn at the desired speed as they advance increases more and more. Progression through the canal further increases the risk of the file becoming blocked or tighten. When this occurs the torque applied to the file increases strongly and there is a risk of the file breaking. File breakage inside the root canal is an outcome the dentist dreads, since the broken point is generally irretrievable.

The endodontic instrument which is the object of Publication No. EP 1 752 109 comprises several, specifically three, spiral flutes defining the concave surfaces whose extremities are located on a circumscribed circle. These extremities constitute the peaks of the instrument's working angles and at least one side of these angles is constituted by the concave flute surfaces. It happens that these angles are all negative or neutral so as to form scraping angles, but never cutting angles, since only positive angles are capable of performing cutting operations. In order to be positive, the tangents to the sides of the angles must be situated on the same side of the radius of the circumscribed circle that corresponds to the peak of the angle. Therefore, this instrument cannot be used as an instrument that cuts sufficiently to form a root canal.

Furthermore, the instruments currently available on the market for implementing the new technique of using mechanically driven files are derived directly from traditional spiral shaped instruments for manual use. This spiral formation is often the source of the tightening and blocking phenomenon that can cause instrument breakage.

Another problem that may occur is that the instrument, instead of following the original shape of the root canal within the sharply curved areas, may have a tendency to carve out its own path or deform the original canal walls when the flute edges are too sharp. One solution consists of blunting the cutting edges of the instrument to a greater or lesser extent in order to prevent them from cutting the material and boring a path that does not correspond to the natural shape of the canal. This can be accomplished by forming an enlarged flat radial area on an endodontic instrument in which there is a large separation between the flute edges. This geometry allows the edges to be blunted, but it has the drawback of increasing working friction and heating the instrument, running the risk of breakage. In addition, enlarging the flat radial area makes the instrument more rigid, resulting in diminished flexibility and an increased risk of uncontrolled deviation within the curved areas of the root canals.

Finally, the walls of a root canal require different treatments along the length of the canal so that the dental surgeon must adapt the instruments according to the desired result. Current instruments do not allow variable treatment sequences to take place throughout the length of the root canal, but require the use of a series of instruments that vary in shape from one instrument to the next.

SUMMARY OF THE INVENTION

The present invention proposes to improve the disadvantages described above and to furnish a means for ensuring effective root canal preparation by placing at the practitioner's disposal an instrument that is sharp enough in the desired areas to form the appropriate root canal, yet blunt enough in the desired areas to avoid cutting the material and comply with the original shape, and flexible enough to follow the sharply curved areas in the canal.

This goal is attained by the instrument of the invention as described below and characterized in that at different levels along the length of the working portion, the cutting angle at the peak of the at least one flute, defined as being the angle formed by the tangents to the peak on the sides of the at least one ridge with the radius of the circle formed by the peak, varies in width in at least one predetermined area on the working portion and is either negative when the tangent to the exterior side of the ridge is located on the side opposite the tangent to the interior side opposite the ridge relative to the radius of the circle, or nil when the tangent to the exterior side of the ridge coincides with the radius of the circle, or positive when the tangent to the exterior side of the ridge is located on the same side as the tangent to the interior side opposite the ridge relative to the radius of the circle, to define along the ridge of the at least one flute either a scraping area or a cutting area, that are either more or less active.

According to a particularly advantageous embodiment in which the instrument comprises three flutes defining three ridges each comprising an edge having a peak and two sides, interior and exterior, respectively, located on either side of the edge at different levels along the length of the working portion, the cutting angles on the respective peaks defined by the tangents to the peaks of the interior sides of the ridges with the respective radii of the circle corresponding to the peaks, can vary in size independently of one another on at least one predetermined zone of the working portion; and are either negative when the tangents to the interior sides of the ridges are located on the side opposite the tangents to the exterior sides opposite the ridges relative to the radii of the circle, or nil when the tangents to the interior sides of the ridges coincide with the radii of the circle, or positive when the tangents to the interior sides of the ridges are located on the same side as the tangents to the exterior sides opposite the ridges relative to the radii of the circle, to define along the edges of the same ridge either a scraping area or a cutting area, that are either more or less active.

According to a preferred form of embodiment, the endodontic instrument comprises at least one zone in which the cutting angle at the respective peak increases progressively from the tip towards the instrument support fitting.

According to another preferred embodiment, the endodontic instrument comprises at least one zone wherein the cutting angle at the respective peak decreases progressively from the tip towards the instrument support fitting.

The endodontic instrument may advantageously comprise several zones distributed along the working portion in which the relief angle at a peak, which is the angle formed by the tangent to the peak on the side of the corresponding ridge with the tangent to this same peak on the circle, the drill bit angle formed by the tangent with the tangent to the side of the same ridge, and the cutting angle are different from one zone to another.

The endodontic instrument may comprise on its working portion at least one zone called the cutting zone.

The endodontic instrument may comprise on its working portion at least one zone called the scraping zone.

The endodontic instrument may comprise on its working portion at least one zone called the neutral zone.

According to other embodiments, the instrument may comprise two or four flutes which define two or four ridges, each comprising an edge supporting a peak, and two sides respectively located on either side of the edge.

BRIEF DESCRIPTION OF THE DRAWINGS

The present invention and its principal advantages will be more readily apparent from the description of different embodiments, with reference to the attached drawings, in which:

FIG. 5AA is an enlarged view of FIG. 5A.

FIG. 6AA is an enlarged view of FIG. 6A.

FIG. 7AA is an enlarged view of FIG. 7A.

FIG. 8AA is an enlarged view of FIG. 8A.

FIG. 9AA is an enlarged view of FIG. 9A.

FIG. 10AA is an enlarged view of FIG. 10A.

FIG. 11AA is an enlarged view of FIG. 11A.

FIG. 12AA is an enlarged view of FIG. 12A.

DETAILED DESCRIPTION OF THE PREFERRED EMBODIMENTS

Figure 1:
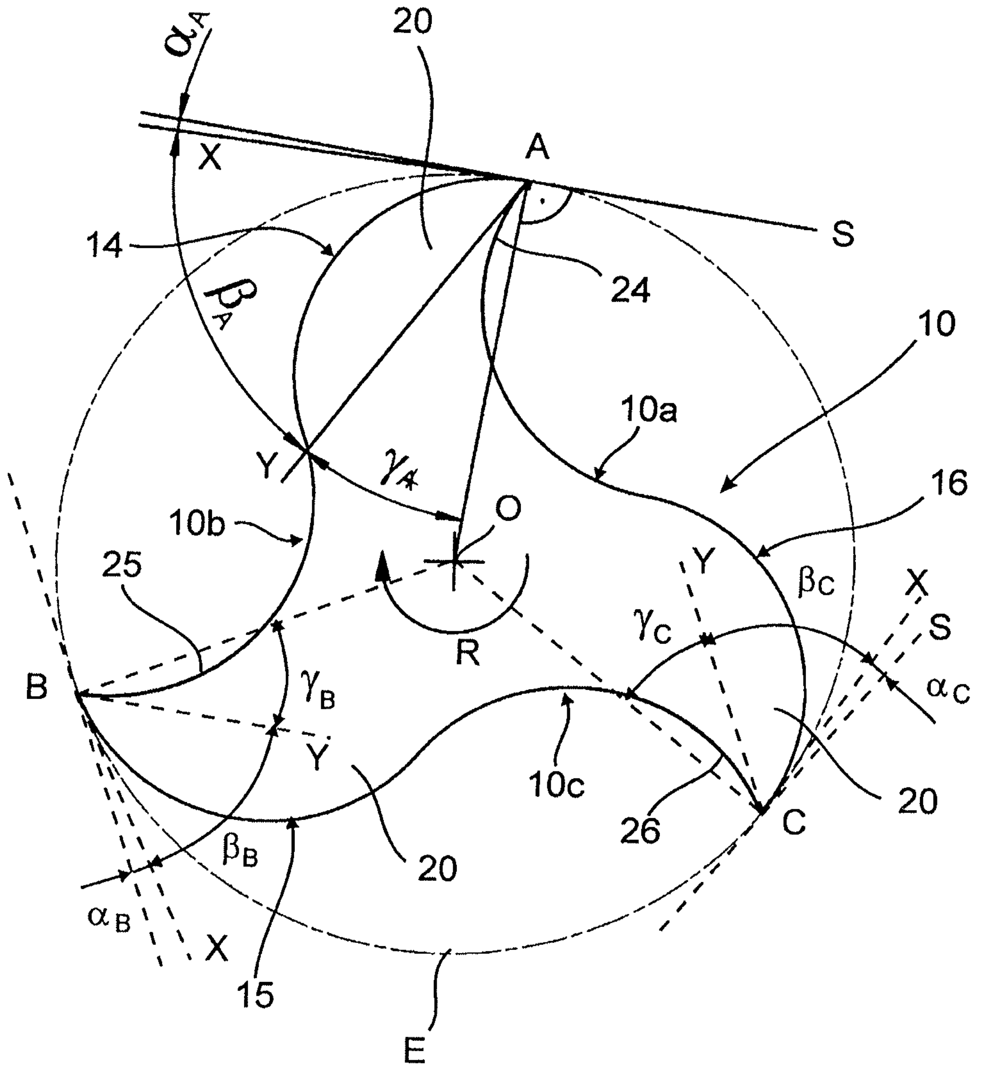
FIG. 1 is a schematic cross-section illustrating a transverse section of a first specific embodiment of the instrument according to the invention.
Figure 9:
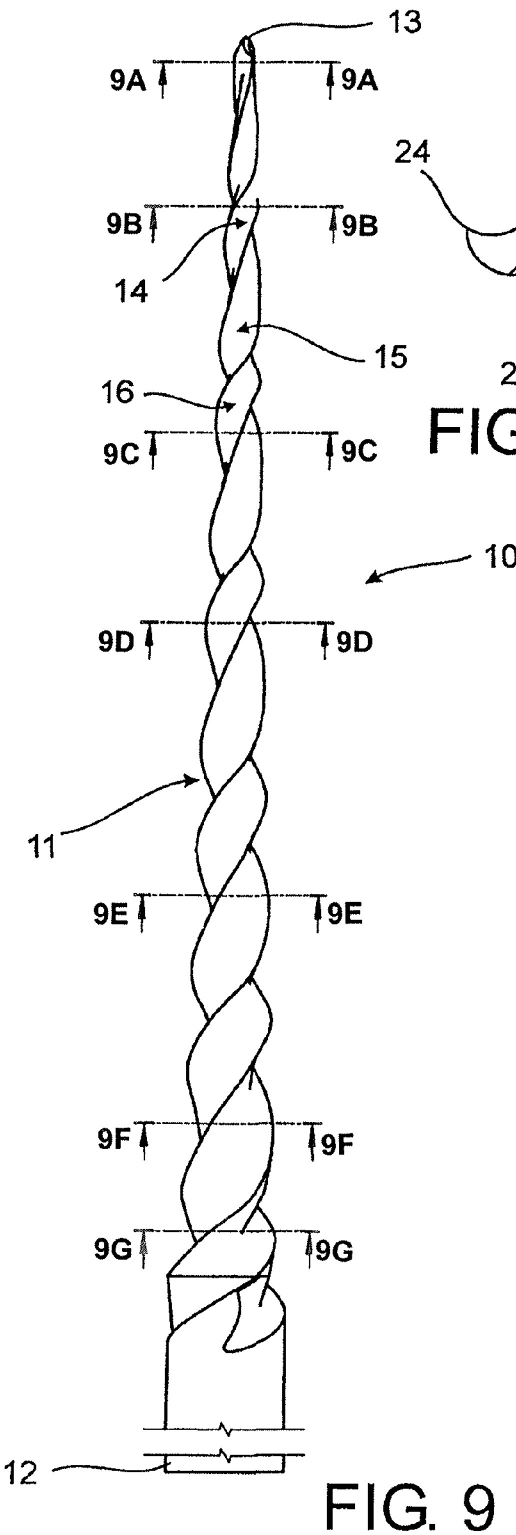
FIG. 9 represents a view of a fifth embodiment of the instrument of the invention.
Figure 9A:
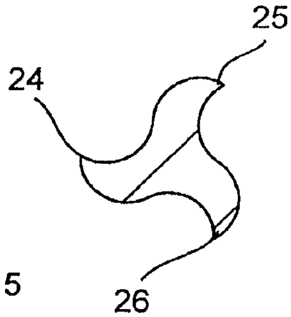
FIG. 9A represents a transverse cross-section of the instrument along section line 9A-9A of FIG. 9 at one level of the working portion of the instrument.
Figure 9A:
Figure 9B:
FIG. 9B represents a transverse cross-section of the instrument along section line 9B-9B of FIG. 9 at another level of the working portion of the instrument.
Figure 9C:
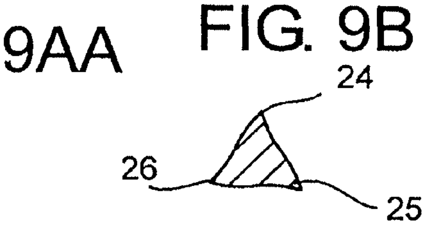
FIG. 9C represents a transverse cross-section of the instrument along section line 9C-9C of FIG. 9 at a further level of the working portion of the instrument.
Figure 9D:
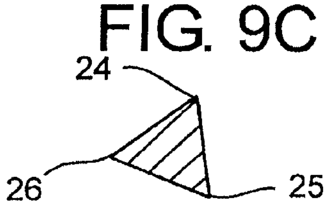
FIG. 9D represents a transverse cross-section of the instrument along section line 9D-9D of FIG. 9 at yet another level of the working portion of the instrument.
Figure 9E:
FIG. 9E represents a transverse cross-section of the instrument along section line 9E-9E of FIG. 9 at still another one level of the working portion of the instrument.
Figure 9F:
FIG. 9F represents a transverse cross-section of the instrument along section line 9F-9F of FIG. 9 at another level of the working portion of the instrument.
Figure 9G:
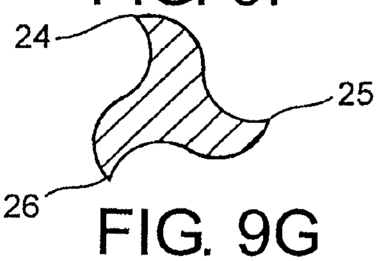
FIG. 9G represents a transverse cross-section of the instrument along section line 9G-9G of FIG. 9 at a yet further level of the working portion of the instrument.
Figure 10:
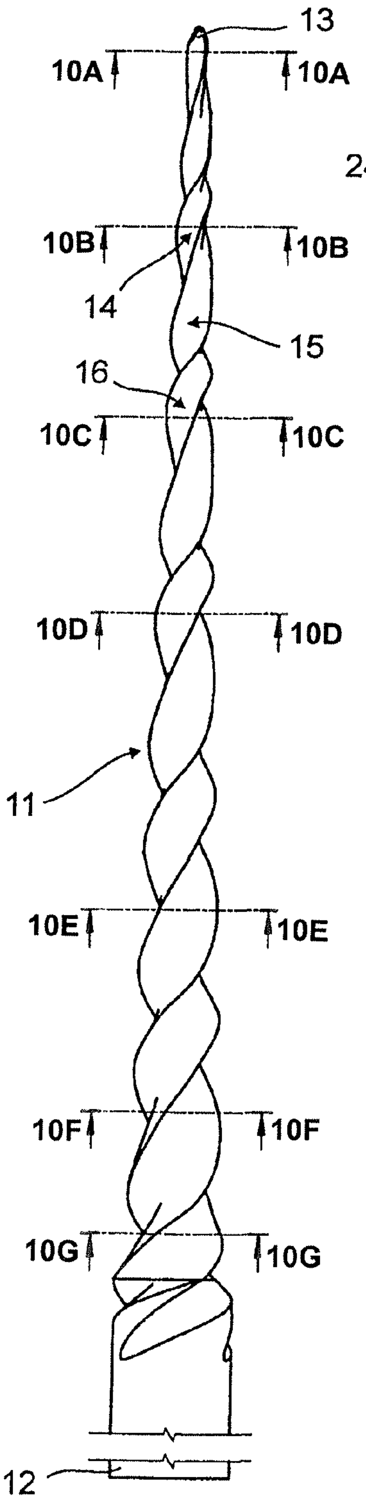
FIG. 10 represents a view of a sixth embodiment of the instrument of the invention.
Figure 10A:
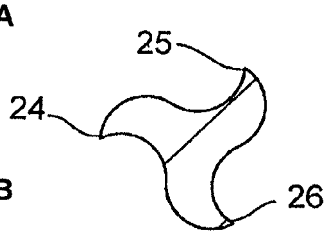
FIG. 10A represents a transverse cross-section of the instrument along section line 10A-10A of FIG. 10 at one level of the working portion of the instrument.
Figure 10A:
Figure 10B:
FIG. 10B represents a transverse cross-section of the instrument along section line 10B-10B of FIG. 10 at another level of the working portion of the instrument.
Figure 10C:
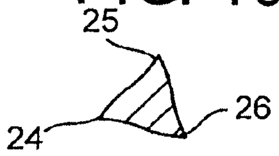
FIG. 10C represents a transverse cross-section of the instrument along section line 10C-10C of FIG. 10 at a further level of the working portion of the instrument.
Figure 10D:
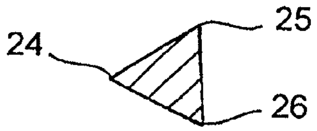
FIG. 10D represents a transverse cross-section of the instrument along section line 10D-10D of FIG. 10 at yet another level of the working portion of the instrument.
Figure 10E:
FIG. 10E represents a transverse cross-section of the instrument along section line 10E-10E of FIG. 10 at another level of the working portion of the instrument.
Figure 10F:
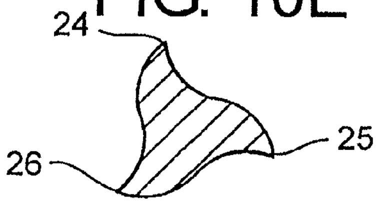
FIG. 10F represents a transverse cross-section of the instrument along section line 10F-10F of FIG. 10 at one more level of the working portion of the instrument.
Figure 10G:
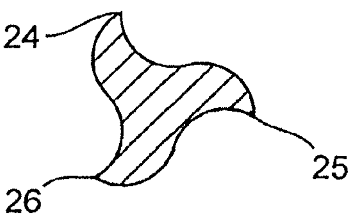
FIG. 10G represents a transverse cross-section of the instrument along section line 10G-10G of FIG.10 at yet a further level of the working portion of the instrument.

FIG. 1 represents a cross-section view along a transverse plane perpendicular to the longitudinal rotational axis of an instrument or endodontic file 10 like the one shown in FIGS. 9 and 10. In this case instrument 10 comprises three spiral flutes 14, 15, 16 defining three ridges 20, the edges 24, 25, 26 of which support peaks A, B and C and three sides 10*a* , 10*b* and 10*c* , interior and exterior, alternately, located on either side of the edges. The transverse cross-section defines a generally triangular portion of peaks A, B and C which are located on a circle E whose center O is located on the longitudinal rotational axis of the instrument. Edges 24, 25, 26 constitute the geometric locations of peaks A, B and C, respectively. The rotational direction of instrument 10 is represented as an arc by arrow R.

Angle $\alpha_A$, called the relief angle at peak A, is defined as being the angle formed by tangent AX in A to exterior side 10*b* of ridge 20, the edge 24 of which supports this peak A, with tangent AS at A, to circumscribed circle E. Similarly, relief angle $\alpha_B$ on peak B can be defined as being the angle formed by tangent BX at B to exterior side 10*c* of ridge 20, the edge 25 of which supports this summit B, with tangent BS at B to circumscribed circle E; and relief angle $\alpha_C$ on peak C as being the angle formed by tangent CX at C to exterior side 10*a* of ridge 20, edge 26 of which supports the peak C, with tangent CS at peak C to circumscribed circle E.

An angle $\beta_A$ at peak A or angle XAY are called the drill bit angle, the angle formed by a second tangent AX at A to exterior side 10*b* of ridge 20, edge 24 of which supports peak A, with a first tangent AY at A to interior side 10*a* on the same ridge, edge 24 of which supports peak A. Similarly, the angle formed by tangent BX at B to exterior side 10*c* of ridge 20, edge 25 of which supports peak B, with tangent BY at B on interior side 10*b* of the same ridge, edge 25 of which supports peak B will be called angle $\beta_B$ or angle XBY; and the angle formed by tangent CX at C on exterior side 10*a* of ridge 20, edge 26 of which supports peak C, with tangent CY at C to interior side 10*c* of the same ridge 20, interior edge 26 of which supports peak C, is called angle $\beta_C$ or angle XCY.

The angle formed by tangent AY at peak A on interior side 10*a* of ridge 20, edge 24 of which supports peak A, with radius AO of circumscribed circle E corresponding to peak A is called cutting angle $\gamma_A$ at A. Similarly, cutting angle $\gamma_B$ at B is the angle formed by tangent BY at peak B on interior side 10*b* of ridge 20, edge 25 of which supports peak B with radius BO corresponding to peak B, and cutting angle $\gamma_C$ at C is the angle formed by tangent CY at peak C on interior side 10*c* of ridge 20, edge 26 of which supports peak C, with radius CO corresponding to peak C.

A cutting angle $\gamma$ is called positive when the tangent to the interior attack side of the ridge 20 concerned is located on the same side as the tangent to the exterior side opposite the ridge relative to the corresponding radius. In the case of angles $\gamma_A$, $\gamma_B$, $\gamma_C$, or YAO, YBO, YCO, respective tangents AY, BY and CY are effectively situated on the same side as tangents AX, BX and CX relative to respective radii AO, BO and CO. The cutting angles called positive and the instrument has an essentially cutting characteristic in the area concerned.

Figure 2:
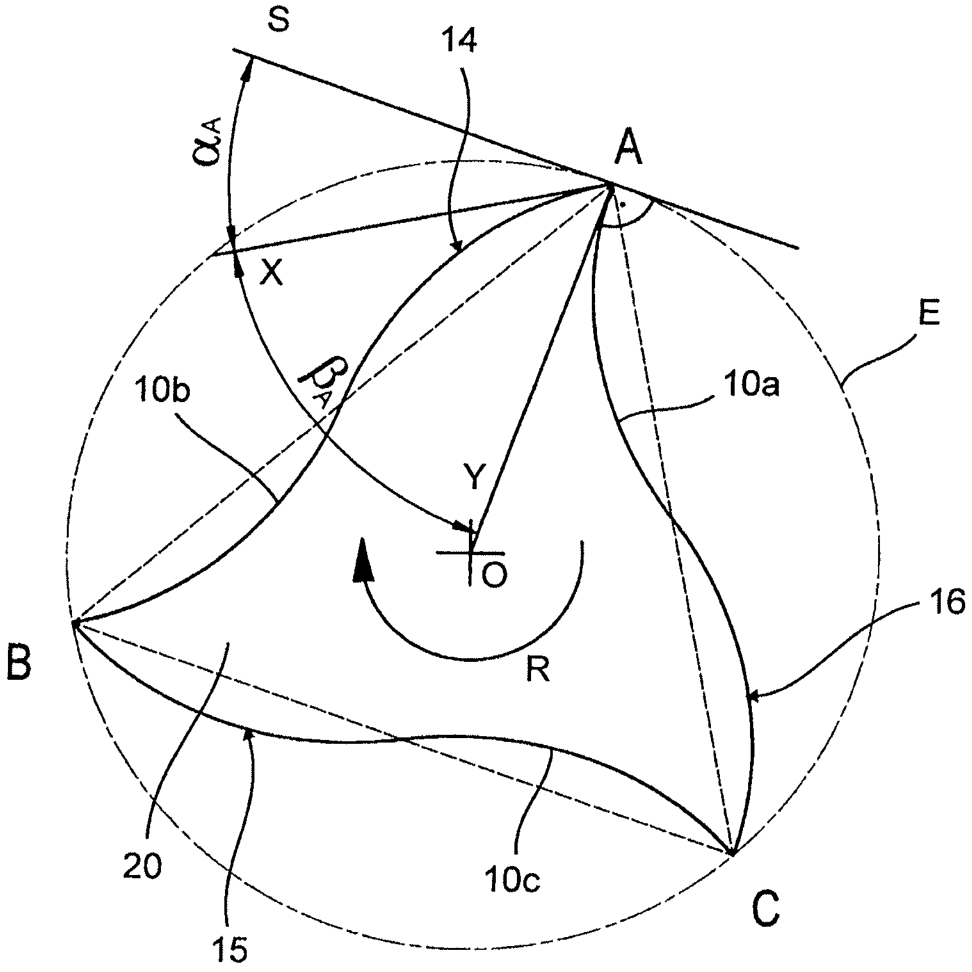
FIG. 2 is a schematic cross-section illustrating a transverse section of a second specific embodiment of the instrument according to the invention.

FIG. 2 is a view similar to that of FIG. 1, but simplified for purposes of clarity. Instrument 10 comprises, as before, three spiral flutes 14, 15, 16. As before, the transverse cross-section defines a generally triangular section of peaks A, B, C which are inscribed in a circumscribed circle E. Flutes 14, 15, 16 define ridges 20, the edges of which are the geometric locations of peaks A, B and C, respectively.

Angle $\alpha_A$, called the relief angle at peak A, is defined as being the angle formed by tangent AX at A to exterior side 10*b* of ridge 20, the edge of which supports the summit A, with tangent AS at A, to circumscribed circle E. Similarly, relief angle $\alpha_B$ at peak B may be defined as being the angle formed by tangent BX at B to exterior side 10*c* of ridge 20, the edge of which supports peak B, with tangent BS at B to circumscribed circle E; and angle relief angle $\alpha_C$ at peak C as being the angle formed by tangent CX at C to exterior side 10*a* of ridge 20, the edge of which supports peak C, with tangent CS at peak C to circumscribed circle E.

Angle $\beta_A$ or angle XAY, the angle formed by tangent AX at A to exterior side 10*b* of ridge 20, the edge of which supports peak A with tangent AY at A to interior side 10*a* of the same ridge 20, the edge of which supports peak A, is called the drill bit angle at peak A. Similarly, the angle formed by tangent BX at B to exterior side 10*c* of ridge 20, the edge of which supports peak B, with tangent B, with tangent BY at B to interior side 10*b* of the same ridge, the edge of which supports peak B will be called angle $\beta_B$ or angle XBY; and the angle formed by tangent CX at C to exterior side 10*a* of ridge 20, the edge of which supports peak C, with tangent CY at C to interior side 10*c* of the same ridge 20, the edge of which supports peak C, will be called angle $\beta_C$ or angle XCY The angle formed by tangent AY at the peak of interior side 10*a* of ridge 20, the edge of which supports peak A, with radius AO corresponding to peak A is called cutting angle $\gamma_A$ at A. Similarly, the angle formed by tangent BY at peak B to interior side 10*b* of ridge 20, the edge of which supports peak B, with radius BO corresponding to peak B is called cutting angle $\gamma_B$ at B; the angle formed by tangent CY at peak C to interior side 10*c* of ridge 20, the edge of which supports peak C with radius CO corresponding to peak C is called cutting angle $\gamma_C$ at C.

In this case cutting angle $\gamma_A$ which defines the orientation of the ridge corresponding to peak A is nil. The edge of the ridge is called neutral. Tangent AY coincides with radius AO.

Figure 3:
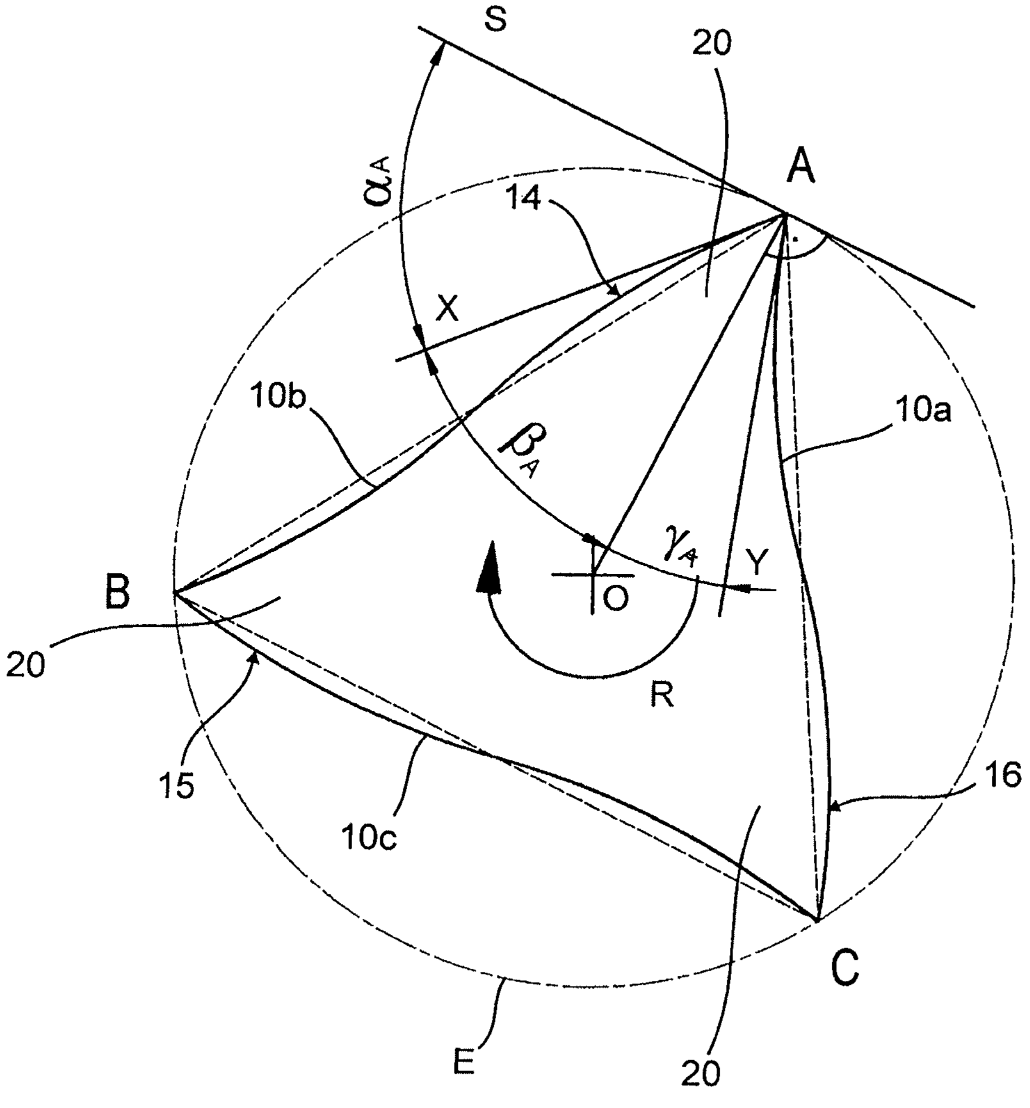
FIG. 3 is a schematic cross-section illustrating a transverse section of a third specific embodiment of the instrument according to the invention.

The area of the instrument represented in FIG. 1 is a tool for cutting the material and the area of the instrument represented in FIG. 2 is a tool for scraping the material. FIG. 3 represents a view similar to that of FIG. 2. Instrument 10 comprises, as before, three spiral flutes 14, 15, 16. As before, the transverse cross-section defines a generally triangular section of peaks A, B and C which are inscribed in a circumscribed circle E. Flutes 14, 15 16 define ridges 20, the edges of which are the geometric locations of peaks A, B and C, respectively.

The drill bit angle, the relief angle and the cutting angle have the same definitions as previously. In this case cutting angle $\gamma_A$ which defines the orientation of the edge corresponding to peak A is negative. The interior tangent to the surface called the attack surface of the ridge 20 concerned is located on the side opposite the tangent to the surface opposite the ridge 20 concerned relative to the corresponding radius AO.

The area of the instrument represented in FIG. 3 is a tool for scraping the material and not a cutting tool.

Figure 4:
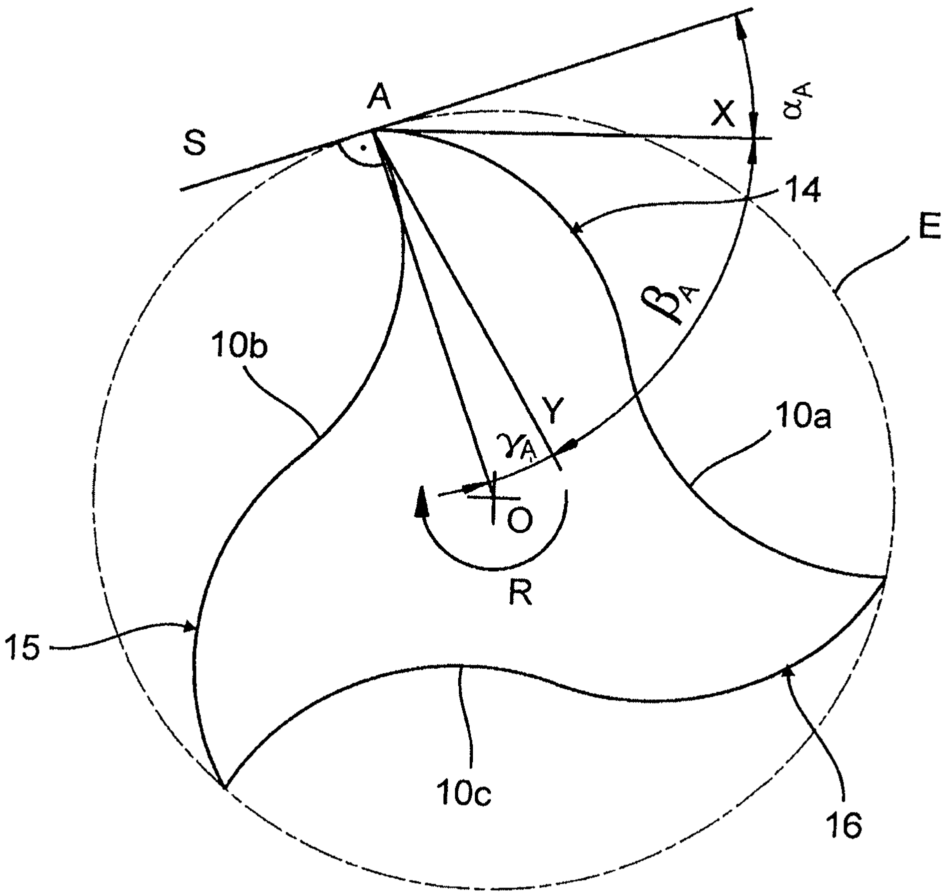
FIG. 4 is a schematic cross-section illustrating a transverse section of a fourth specific embodiment of the instrument according to the invention.

FIG. 4 represents a view similar to those of FIGS. 2 and 3. Instrument 10 comprises as before three spiral flutes 14, 15 and 16. As before, the transverse cross-section defines a generally triangular section of peaks A, B and C which are inscribed in a circumscribed circle E. The flutes define ridges, the edges of which are the geometric locations of peaks A, B and C, respectively. Angle $\alpha_A$, called the relief angle at peak A, is defined as being the angle formed by tangent AX to peak A on the exterior surface of side 10*a* with the perpendicular to radius AO of circumscribed circle E, or the tangent AS at peak A relative to circumscribed circle E.

The drill bit angle, the relief angle and the cutting angle have the same definitions as before. In this case, cutting angle $\gamma_A$ which defines the orientation of the edge corresponding to peak A is positive. Tangent AX to the surface called the attack surface on the ridge 20 concerned is situated on the same side as tangent AY to opposing surface 10*bde* of the ridge 20 concerned relative to corresponding radius AO. In light of the orientation of the attack surface relative to the direction of rotation R, the area of the instrument shown in transverse cross-section is an instrument for scraping.

Figure 5:
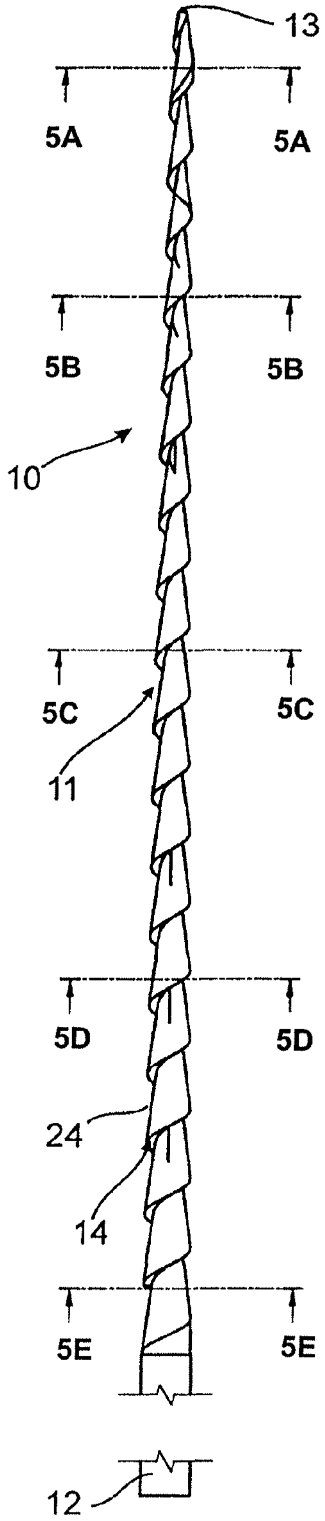
FIG. 5 is an overall view of one embodiment of the instrument according to the invention.

With reference to FIG. 5, endodontic instrument or file 10 comprises a portion called the working portion 11 and a securing end fitting 12 for mounting the instrument in a supporting counter-angle type mandrel equipped with an electric motor driving it clockwise. In this example, the entire length of the casing of working portion 11 is conical and terminates in a tip 13, the securing end fitting 12 being cylindrical to ensure that it remains inside the mandrel (not shown). In this embodiment, working portion 11 is equipped with a single spiral flute 14 forming a ridge 20 with an edge, the cutting edge 24.

Figure 5A:
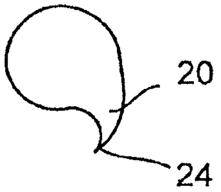
FIG. 5A represents a transverse cross-section of the instrument along section line 5A-5A of FIG. 5 at one level of the working portion of the instrument.
Figure 5A:
Figure 5B:
FIG. 5B represents a transverse cross-section of the instrument along section line 5B-5B of FIG. 5 at another level of the working portion of the instrument.
Figure 5C:
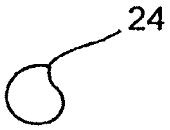
FIG. 5C represents a transverse cross-section of the instrument along section line 5C-5C of FIG. 5 at yet another level of the working portion of the instrument.
Figure 5D:
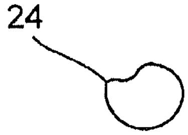
FIG. 5D represents a transverse cross-section of the instrument along section line 5D-5D of FIG. 5 at a further level of the working portion of the instrument.
Figure 5E:
FIG. 5E represents a transverse cross-section of the instrument along section line 5E-5E of FIG. 5 at yet a further level of the working portion of the instrument.

In this embodiment cross-sectional views 5A through 5E taken along the cross-sections respectively designated by 5A-5A; 5B-5B; 5C-5C; 5D-5D and 5E-5E, as well as the enlarged view in FIG. 5AA, show the disposition of edge 24. Apart from the fact that instrument 10 comprises only a single flute 14, this embodiment corresponds to the instrument described with reference to FIG. 1. The instrument is a cutting tool with a positive cutting angle $\gamma$ in the portion near tip 13, but which may vary along the length of working portion 11.

It should be noted that drill bit angle $\beta$, relief angle $\alpha$ and cutting angle $\gamma$ may vary along the entire length of working portion 11. In the present case, the instrument is particularly sharp in the area near tip 13 and the profile of cutting edge 24 becomes progressively more blunt along the length of instrument 10.

Figure 6:
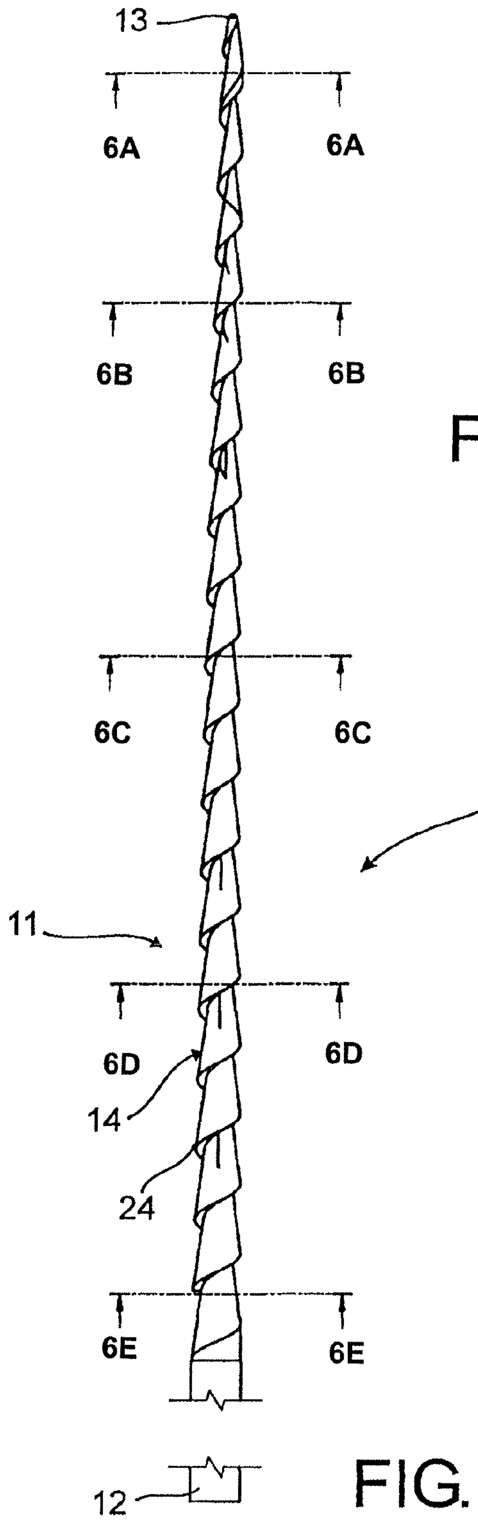
FIG. 6 represents a view of another embodiment of the instrument according to the invention.

In the following description, identical elements bear the same reference numerals. Instrument 10 shown in FIG. 6 comprises, as before, a working portion 11 with a generally parallelepiped section, and a securing end fitting 12 for mounting the instrument in a mandrel driven by an electric motor. In this embodiment, as in the case shown in FIG. 5, working portion 11 is equipped with a single spiral flute 14 forming an edge, the cutting edge 24.

Figure 6A:
FIG. 6A represents a transverse cross-section of the instrument along section line 6A-6A of FIG. 6 at one level of the working portion of the instrument.
Figure 6A:
Figure 6B:
FIG. 6B represents a transverse cross-section of the instrument along section line 6B-6B of FIG. 6 at another level of the working portion of the instrument.
Figure 6C:
FIG. 6C represents a transverse cross-section of the instrument along section line 6C-6C of FIG. 6 at yet another one level of the working portion of the instrument.
Figure 6D:
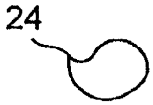
FIG. 6D represents a transverse cross-section of the instrument along section line 6D-6D of FIG. 6 at a further level of the working portion of the instrument.
Figure 6E:
FIG. 6E represents a transverse cross-section of the instrument along section line 6E-6E of FIG. 6 at still a further level of the working portion of the instrument.

In this embodiment the transverse cross-sectional views 6A through 6E taken along the cross-sections respectively designated by 6A-6A; 6B-6B; 6C-6C; 6D-6D and 6E-6E, as well as the enlarged view in FIG. 6AA, show the disposition of edge 24. Apart from the fact that instrument 10 comprises only a single flute 14, this embodiment corresponds to the instrument described with reference to FIG. 1. The instrument is a cutting instrument with a negative cutting angle $\gamma$ in the area near tip 13, but the angle may vary along the length of working portion 11.

As in the preceding example, note that drill bit angle $\beta$, relief angle $\alpha$ and cutting angle $\gamma$ may vary along the entire length of working portion 11. In the present case, the instrument is a scraper in the area near tip 13 and the profile of cutting edge 24 becomes progressively finer along the length of instrument 10 until it becomes a cutting edge in the vicinity of securing end fitting 12 where the instrument functions as a cutter.

Figure 7:
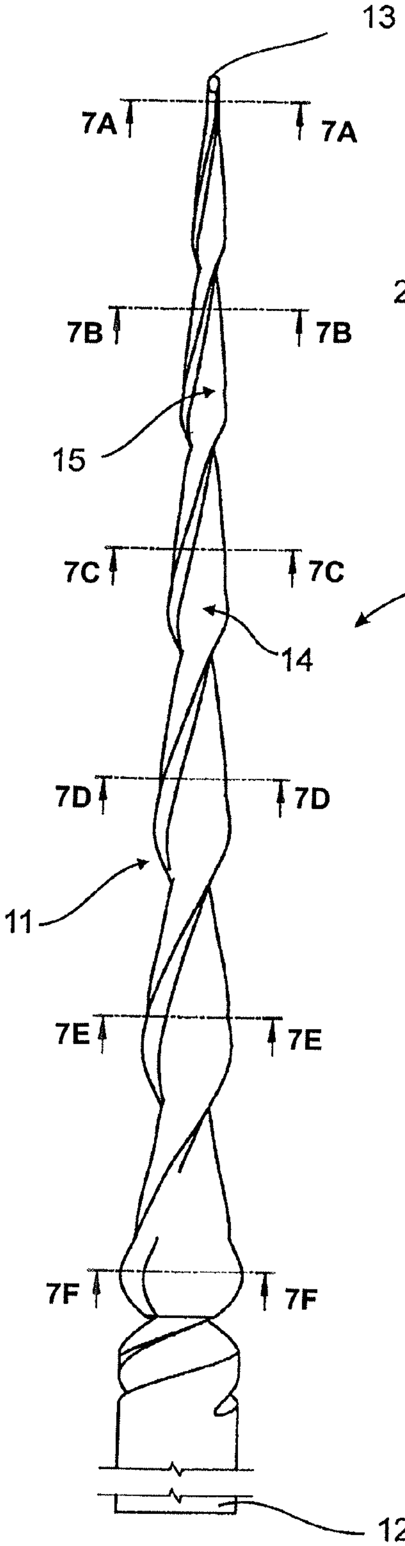
FIG. 7 represents a view of another embodiment of the instrument according to the invention.
Figure 7A:
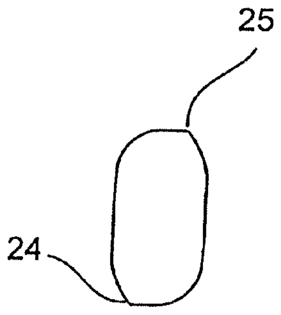
FIG. 7A represents a transverse cross-section of the instrument along section line 7A-7A of FIG. 7 at one level of the working portion of the instrument.
Figure 7A:
Figure 7B:
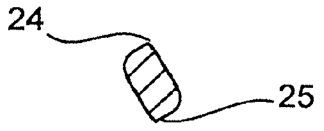
FIG. 7B represents a transverse cross-section of the instrument along section line 7B-7B of FIG. 7 at another level of the working portion of the instrument.
Figure 7C:
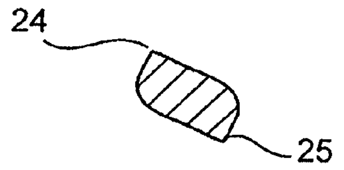
FIG. 7C represents a transverse cross-section of the instrument along section line 7C-7C of FIG. 7 at a further level of the working portion of the instrument.
Figure 7D:
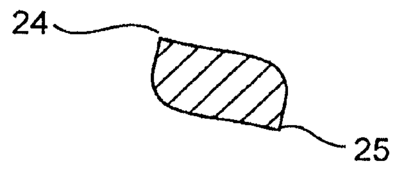
FIG. 7D represents a transverse cross-section of the instrument along section line 7D-7D of FIG. 7 at yet another level of the working portion of the instrument.
Figure 7E:
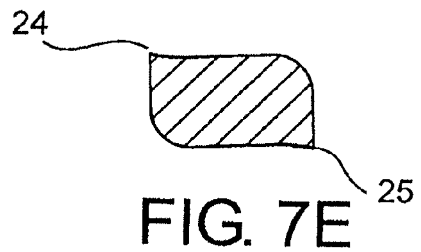
FIG. 7E represents a transverse cross-section of the instrument along section line 7E-7E of FIG. 7 at still another level of the working portion of the instrument.
Figure 7F:
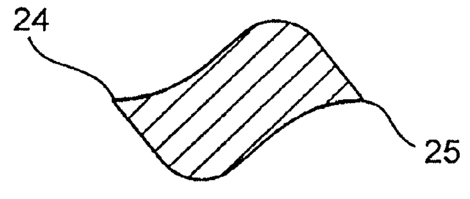
FIG. 7F represents a transverse cross-section of the instrument along section line 7F-7F of FIG. 7 at yet a further level of the working portion of the instrument.

Instrument 10 shown in FIG. 7 is more or less rectangular in section and comprises two spiral flutes 14 and 15 generally symmetrically disposed along the entire length of working portion 11. It will be noted from observing the transverse lines all along working portion 11, that instrument 10 is essentially a scraping tool in the area of tip 13 and is progressively transformed into a cutting tool approaching the securing end fitting 12. Cutting edges 24 and 25 of flutes 14 and 15 are relatively blunt near tip 13 and become progressively sharper near securing end fitting 12.

Figure 8:
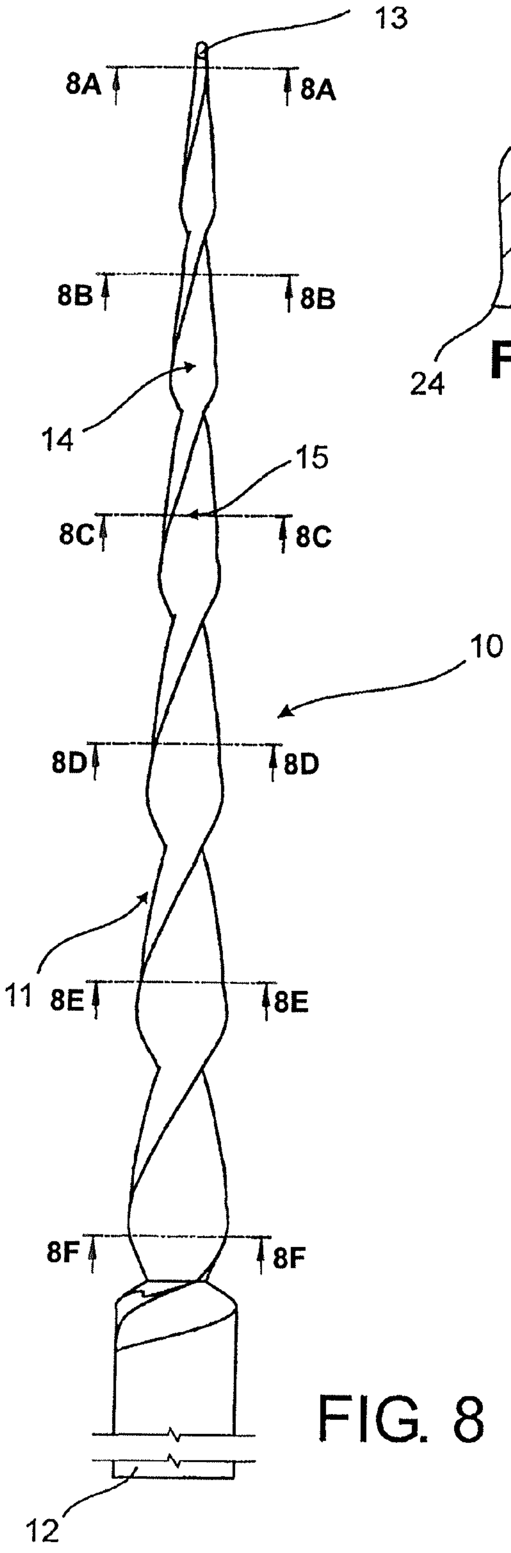
FIG. 8 represents a view of a fourth embodiment of the instrument according to the invention.
Figure 8A:
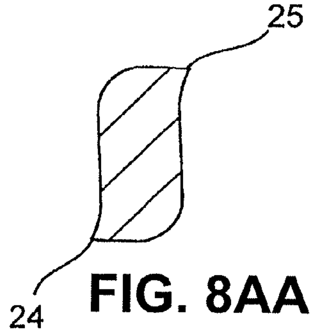
FIG. 8A represents a transverse cross-section of the instrument along section line 8A-8A of FIG. 8 at one level of the working portion of the instrument.
Figure 8A:
Figure 8B:
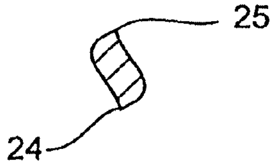
FIG. 8B represents a transverse cross-section of the instrument along section line 8B-8B of FIG. 8 at another level of the working portion of the instrument.
Figure 8C:
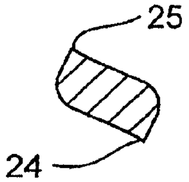
FIG. 8C represents a transverse cross-section of the instrument along section line 8C-8C of FIG. 8 at a further level of the working portion of the instrument.
Figure 8D:
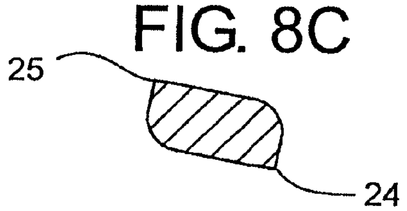
FIG. 8D represents a transverse cross-section of the instrument along section line 8D-8D of FIG. 8 at yet another level of the working portion of the instrument.
Figure 8E:
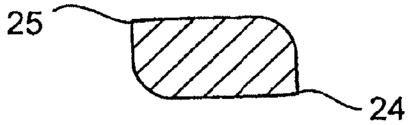
FIG. 8E represents a transverse cross-section of the instrument along section line 8E-8E of FIG. 8 at a still further level of the working portion of the instrument.
Figure 8F:
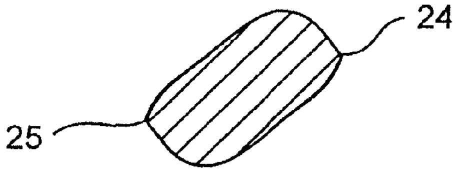
FIG. 8F represents a transverse cross-section of the instrument along section line 8F-8F of FIG. 8 at yet a further level of the working portion of the instrument.

Instrument 10 shown in FIG. 8 is similar to the one shown in FIG. 7 and is more or less rectangular in section, comprising two spiral flutes 14 and 15 generally symmetrically disposed along the entire length of working portion 11. It will be noted from observing the transverse lines all along working portion 11 that the present instrument 10, in contrast to the instrument of FIG. 7, is essentially a cutting tool near tip 13 and is progressively transformed into a scraping tool approaching the securing end fitting 12. Cutting edges 24 and 25 of flutes 14 and 15 are relatively sharp near tip 13 and become progressively more blunt towards securing end fitting 12.

FIGS. 9 and 10 represent two embodiments of instrument 10 in which the portion called the working portion 11 comprises three spiral flutes 14, 15, 16 defining three edges 24, 25 and 26.

On instrument 10 shown in FIG. 9, edges 24, 25 and 26 are first, cutting edges and then become scraping edges; and on instrument 10 shown in FIG. 10, the edges are first, scraping edges and then become cutting edges as they are displaced from tip 13 towards securing end fitting 12. The drill bit, relief and cutting angles may vary independently of one another and all along working portion 11. The drill bit angle, which is the angle formed by the tangents to the two surfaces of a single edge, defines to some extent the fineness of the cutting operation and the cutting capacity of the instrument, but also the flexibility of the area of the instrument in question. In actuality, the finer the instrument, that is, the smaller its transverse section surface, the greater its flexibility. The possibility of modulating the drill bit, relief and cutting angles allows the instrument to be adapted to the practitioner's needs through areas distributed along the length of its working area.

Figure 11:
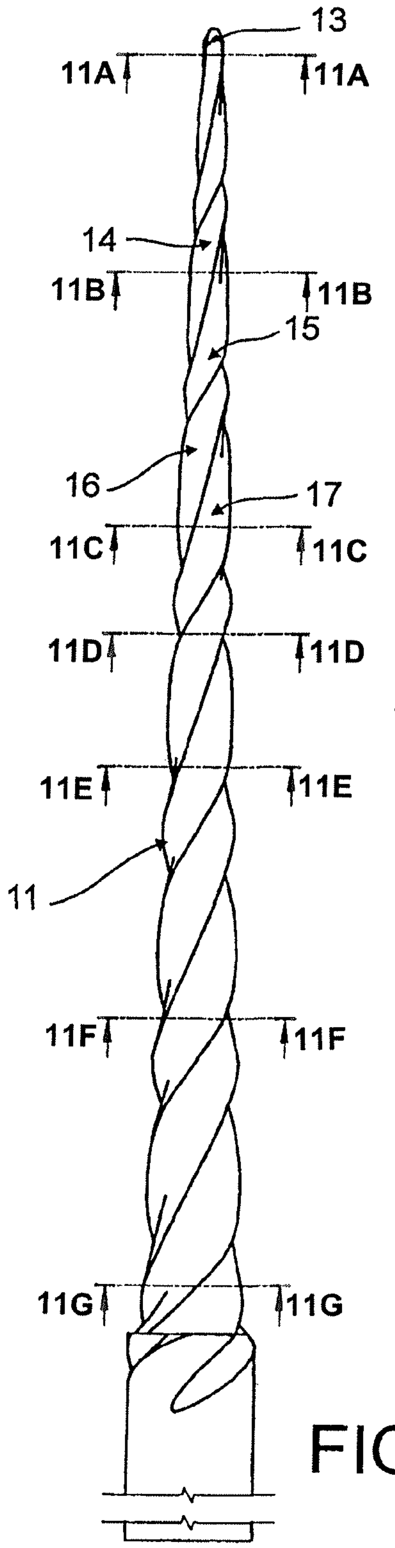
FIG. 11 represents a view of a seventh embodiment of the instrument of the invention.
Figure 11A:
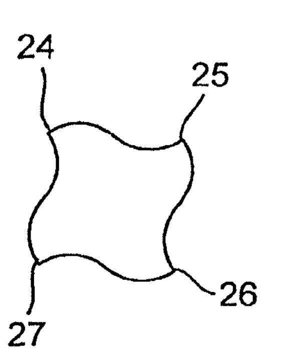
FIG. 11A represents a transverse cross-section of the instrument along section line 11A-11A of FIG. 11 at one level of the working portion of the instrument.
Figure 11A:
Figure 11B:
FIG. 11B represents a transverse cross-section of the instrument along section line 11B-11B of FIG. 11 at another level of the working portion of the instrument.
Figure 11C:
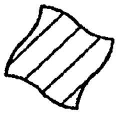
FIG. 11C represents a transverse cross-section of the instrument along section line 11C-11C of FIG. 11 at a further level of the working portion of the instrument.
Figure 11D:
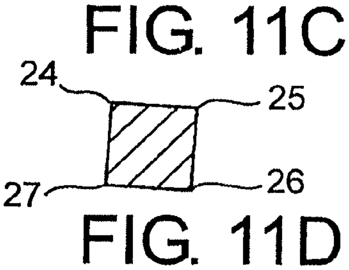
FIG. 11D represents a transverse cross-section of the instrument along section line 11D-11D of FIG. 11 at yet another level of the working portion of the instrument.
Figure 11E:
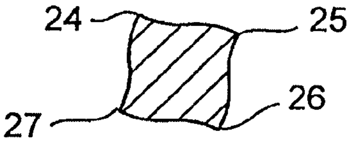
FIG. 11E represents a transverse cross-section of the instrument along section line 11E-11E of FIG. 11 at another level of the working portion of the instrument.
Figure 11F:
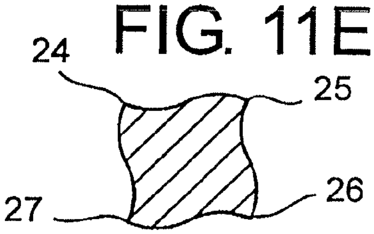
FIG. 11F represents a transverse cross-section of the instrument along section line 11F-11F of FIG. 11 at yet a further level of the working portion of the instrument.
Figure 11G:
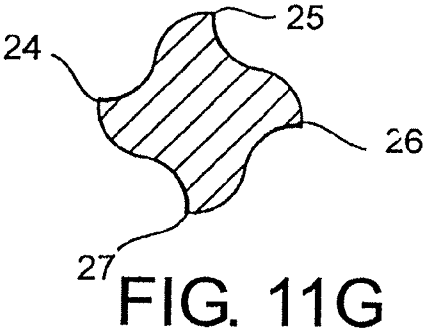
FIG. 11G represents a transverse cross-section of the instrument along section line 11G-11G of FIG. 11 at one more level of the working portion of the instrument.
Figure 12:
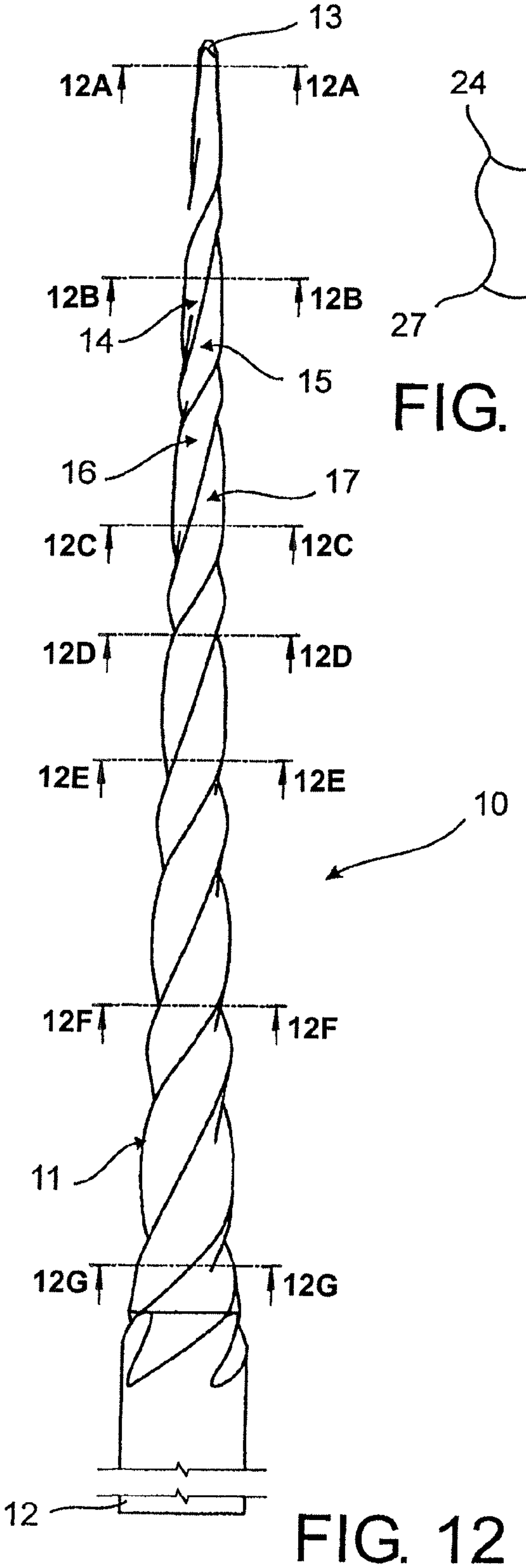
FIG. 12 represents a view of an eighth embodiment of the instrument of the invention.
Figure 12A:
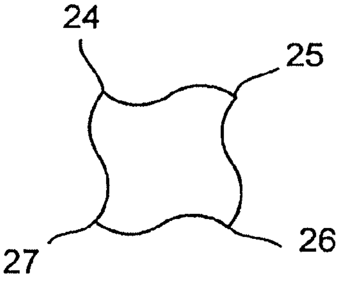
FIG. 12A represents a transverse cross-section of the instrument along section line 12A-12A of FIG. 12 at one level of the working portion of the instrument.
Figure 12A:
Figure 12B:
FIG. 12B represents a transverse cross-section of the instrument along section line 12B-12B of FIG. 12 at another level of the working portion of the instrument.
Figure 12C:
FIG. 12C represents a transverse cross-section of the instrument along section line 12C-12C of FIG. 12 at a further level of the working portion of the instrument.
Figure 12D:
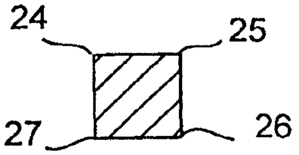
FIG. 12D represents a transverse cross-section of the instrument along section line 12D-12D of FIG. 12 at yet another level of the working portion of the instrument.
Figure 12E:
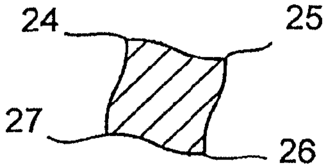
FIG. 12E represents a transverse cross-section of the instrument along section line 12E-12E of FIG. 12 at another level of the working portion of the instrument.
Figure 12F:
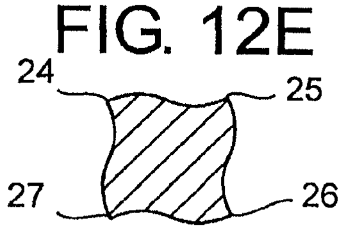
FIG. 12F represents a transverse cross-section of the instrument along section line 12F-12F of FIG. 12 at one more level of the working portion of the instrument.
Figure 12G:
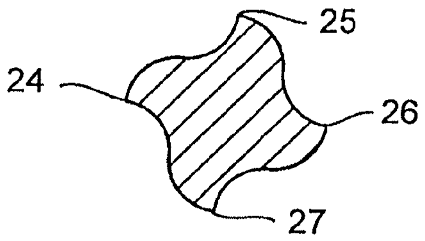
FIG. 12G represents a transverse cross-section of the instrument along section line 12G-12G of FIG. 12 at yet a further level of the working portion of the instrument.

FIGS. 11 and 12 are views illustrating an instrument comprising four flutes 14, 15, 16 and 17 which define four ridges having respectively the four edges 24, 25, 26 and 27 of the transverse cross-sections represented by cross-sections 11A through 11G and 11AA, as well as 12A through 12G and 12AA. In the portion near tip 13 the instrument 10 of FIG. 11 is a scraping tool that progressively becomes a cutting tool towards securing end fitting 12. On instrument 10 in FIG. 12, the instrument is first a cutting tool near tip 13 and is progressively transformed into a scraping tool towards securing end fitting 12.

These variations offer the practitioner the opportunity of adapting the different instruments to the treatment sequences being performed, and during a sequence, to the geometry of the patient's root canal.

The present invention is not limited to the preferred embodiments described, but may undergo different modifications or variations obvious to a person skilled in the art. In particular, on the same instrument, the geometry of the edges may be modulated by passing from a scraping and/or smoothing function to a cutting function, then returning to a scraping function, or conversely, along the entire length of the working portion.

Furthermore, the instrument may comprise a larger number of flutes, specifically spiral flutes. This number is limited only by the transverse dimensions of the instrument.

The invention claimed is:

1. A flexible endodontic instrument for drilling root canals, the instrument (10) having a longitudinal rotational axis and comprising:

a working portion (11) terminating in a tip (13), at one extremity thereof, while an opposite extremity thereof terminating in a securing end fitting (12) which is attachable to a mandrel driven by an electric motor;

the working portion (11) comprising at least one spiral flute (14) that defines a ridge (20), the ridge (20) comprising an edge (24) with a peak (A) between an interior side (10*a*) and an exterior side (10*b*);

only the peak (A) of the edge (24) being situated on a circle (E) whose center (O) is located on the longitudinal rotational axis, at different levels along a longitudinal length of the working portion (11) while a remainder of the ridge (20) being located within and spaced from the circle (E);

the edge (24) having a cutting angle ($y_A$) at the peak (A) of the at least one flute (14) which is defined as being the angle formed by a first tangent (AY) at the peak (A) to the interior side (10*a*) of the ridge (20) and a second tangent (AX) at the peak (A) to the exterior side (10*b*) of the ridge (20);

the cutting angle ($y_A$) varying in width on at least one predetermined area of the working portion (11) such that:

at least a portion along the longitudinal length of the working portion (11) comprising a negative cutting angle, at least a portion along the longitudinal length of the working portion (11) comprising a nil cutting angle, and at least a portion along the longitudinal length of the working portion (11) comprising a positive cutting angle;

the cutting angle being negative when the first tangent (AY) to the interior side (10*a*) of the ridge (20) is located on a side opposite to the second tangent (AX) to the exterior side (10*b*) of the ridge (20) relative to a radius (AO) of the circle (E) joining the center (O) to the peak (A);

the cutting angle ($y_A$) being nil when the first tangent (AY) to the interior side (10*a*) of the ridge (20) coincides with the radius (AO) of the circle (E);

the cutting angle ($y_A$) being positive when the first tangent (AY) to the interior side (10*a*) of the ridge (20) is located on the same side as the second tangent (AX) to the exterior side (10*b*) of the ridge (20) relative to the radius (AO) of the circle (E) joining the center (O) to the peak (A), to define, along the ridge (20) of the at least one flute, either a scraping zone or a cutting zone, active either for scraping or cutting the root canal.

2. The endodontic instrument according to claim 1, the instrument (10) comprising:

three spiral flutes (14, 15, 16), each defining a respective ridge (20);

each of the respective ridges (20) comprises a respective edge (24, 25, 26) with a respective peak (A, B, C) located between respective interior and exterior sides (10*a*, 10*b*; 10*b*, 10*c*; 10*c*, 10*a*), at different levels along the working portion (11);

respective cutting angles ($y_A$,$y_B$,$y_C$) of the respective peaks (A, B, C), are defined by respective first and second tangents (AY, BY, CY, AX, BX, CX) to the respective peaks (A, B, C) of the respective interior sides (10*a*, 10*b*, 10*c*) of the respective ridges (20) with respective radii (AO, BO, CO) of respective circles (E) corresponding to the respective peaks (A, B, C);

the respective cutting angles ($y_A$, $y_B$, $y_C$) vary in size independently of one another, in at least one predetermined area on the working portion (11);

the respective cutting angles ($y_A$, $y_B$,$y_C$) are negative when the respective first tangents (AY, BY, CY) to the respective interior sides of the respective ridges (20) are located opposite the respective second tangents (AX, BX, CX) to the respective interior sides of the respective ridges relative to the respective radii (AO, BO, CO) of the respective circle;

the respective cutting angles ($y_A$, $y_B$, $Y_C$) are nil when the first respective tangents (AY, BY, CY) to the interior respective sides of the respective ridges (20) coincide with the respective radii (AO, BO, CO) of the respective circle; and the respective cutting angles ($y_A$, $y_B$, $y_C$) are positive when the first respective tangents (AY, BY, CY) to the interior respective sides of the ridges (20) are located on the same side as the second respective tangents (AX, BX, CX) to the exterior respective sides (10,10*c*, 10*a*) of the respective ridges (20) relative to the respective radii (AO, BO, CO) of the respective circle, to define along the respective edges of the same respective ridge either a scraping zone or a cutting zone active either for scraping or cutting the root canal.

3. The endodontic instrument according to claim 2, wherein the instrument comprises at least one area in which the respective cutting angles ($y_A$, $y_B$, $y_C$) of the respective peaks (A, B, C) increase progressively from the tip (13) toward the securing end fitting (12).

4. The endodontic instrument according to claim 2, wherein the instrument comprises at least one area in which the respective cutting angles ($y_A$, $y_B$, $y_C$) at the respective peaks (A,B,C), progressively decrease from the tip (13) toward the securing end fitting (12).

5. The endodontic instrument according to claim 1, wherein the instrument comprises several areas, including a first area and a second area, distributed along the working portion (11) in which;

a relief angle ($\alpha_A$) is defined as being the angle formed by the second tangent (AX) at the peak (A) to the exterior side (10*b*) of the ridge (20) of the peak (A) with a third tangent (AS) at the same peak (A) to the circle (E);

a drill bit angle ($\beta_A$) is defined as being the angle formed by the second tangent (AX) with the first tangent (AY) to the interior side (10*a*) of the ridge (20); and the relief angle, ($\alpha_A$) the drill bit angle ($\beta_A$) and the cutting angle ($y_A$) are different from the first area to the second area distributed along the working portion.

6. The endodontic instrument according to claim 1, wherein the working portion (11) comprises at least one cutting area.

7. The endodontic instrument according to claim 1, wherein the working portion (11) comprises at least one scraping area.

8. The endodontic instrument according to claim 1, wherein the working portion comprises at least one neutral area.

9. The endodontic instrument according to claim 1, wherein the instrument comprises two flutes (14, 15) that respectively define two ridges (20), and each respetive ridge comprises an edge (24, 25) supporting a peak and two sides respectively located on either side of the edge (24, 25).

10. The endodontic instrument according to claim 1, wherein the instrument comprises three flutes (14, 15, 16) which respectively define three ridges (20), and each respective ridge comprises a respective edge (24, 25, 26) supporting a respective peak and two sides respectively located on either side of the respective edge (24, 25; 25, 26; 26, 24).

11. The endodontic instrument according to claim 1, wherein the instrument comprises four flutes (14, 15, 16, 17) which respectively define four ridges (20), and each respective ridge comprises an edge (24, 25, 26, 27) supporting a peak and two sides respectively located on either side of the edge (24, 25, 26, 27).

12. A flexible endodontic instrument for drilling root canals, the instrument (10) having a longitudinal rotational axis and comprising:

a working portion (11) terminating in a tip (13), at one extremity thereof, while an opposite extremity thereof terminating in a securing end fitting (12) which is attachable to a mandrel driven by an electric motor;

the working portion (11) comprising a plurality of spiral flutes (14) that each respectively defines a ridge (20);

each of the plurality of ridges (20) extending continuously from the tip (13) to the securing end fitting (12);

each of the plurality of ridges (20) comprising an edge (24) with a peak (A) located between an interior side (10*a*) and an exterior side (10*b*), respectively;

for each of the plurality of ridges (20);

only the peak (A) of the edge (24) being situated on a circle (E) whose center (O) is located on the longitudinal rotational axis, at different levels along the longitudinal length of the working portion (11), while a remainder of the at least one ridge (20) being located within and spaced from the circle (E);

the edge (24) having a cutting angle ($y_A$) at the peak (A) which is defined as being the angle formed by a first tangent (AY) at the peak (A) to the interior side (10*a*) of each of the plurality of ridges (20) and a second tangent (AX) at the peak (A) to the exterior side (10*b*) of each of the plurality of ridges (20);

the cutting angle ($y_A$) varying in width on at least one predetermined area of the working portion (11) such that at least a portion along the longitudinal length of the working portion (11) comprising a negative cutting angle, at least a portion along the longitudinal length of the working portion (11) comprising a nil cutting angle, and at least a portion along the longitudinal length of the working portion (11) comprising a positive cutting angle;

the cutting angle being negative when the first tangent (AY) to the interior side (10*a*) of each of the plurality of ridges (20) is located on a side opposite to the second tangent (AX) to the exterior side (10*b*) of each of the plurality of ridges (20) relative to a radius (AO) of the circle (E) joining the center (O) to the peak (A);

the cutting angle ($y_A$) being nil when the first tangent (AY) to the interior side (10*a*) of each of the plurality of ridges (20) coincides with the radius (AO) of the circle (E); and the cutting angle ($y_A$) being positive when the first tangent (AY) to the interior side (10*a*) of each of the plurality of ridges (20) is located on the same side as the second tangent (AX) to the exterior side (10*b*) of each of the plurality of ridges (20) relative to the radius (AO) of the, circle (E) joining the center (O) to the peak (A), and the cutting angle ($y_A$) defines, along each of the plurality of ridges (20) of each of the plurality of flutes respectively either a scraping zone or a cutting zone, that are active either for scraping or cutting the root canal.

* * * * *